US005687709A

United States Patent [19]

Akerberg

[11] Patent Number: 5,687,709
[45] Date of Patent: Nov. 18, 1997

[54] VENTILATOR ANESTHETIC SYSTEM HAVING A MANUALLY OPERATED SAFETY VALVE DEVICE

[75] Inventor: Leif Akerberg, Jaerfaella, Sweden

[73] Assignee: Siemens Elema AB, Solna, Sweden

[21] Appl. No.: 440,477

[22] Filed: May 12, 1995

[30] Foreign Application Priority Data

May 26, 1994 [SE] Sweden ............... 9401809

[51] Int. Cl.[6] ........................... A61M 15/00
[52] U.S. Cl. ........................ 128/203.12; 128/203.16; 128/203.24; 128/203.25; 128/205.24
[58] Field of Search ............. 128/203.12, 203.16, 128/203.24, 203.25, 205.24; 137/630.15; 251/325, 900

[56] References Cited

U.S. PATENT DOCUMENTS

| | | | |
|---|---|---|---|
| 1,870,293 | 8/1932 | Miller | 137/630.15 |
| 2,593,101 | 4/1952 | Campbell | 137/630.15 |
| 3,032,063 | 5/1962 | Wells | 137/630.15 |
| 3,211,419 | 10/1965 | Klinger-Lohr | 137/630.15 |
| 3,961,645 | 6/1976 | Kagan | 137/630.15 |
| 4,304,264 | 12/1981 | McClintock et al. | 137/630.15 |
| 4,699,173 | 10/1987 | Röhling | 128/203.25 |
| 5,159,924 | 11/1992 | Cegielski et al. | 128/203.25 |
| 5,398,714 | 3/1995 | Price | 128/205.24 |

FOREIGN PATENT DOCUMENTS

| | | | |
|---|---|---|---|
| 4720891 | 12/1970 | Japan | 137/630.15 |
| WO90/01965 | 3/1990 | WIPO | |

Primary Examiner—Aaron J. Lewis
Attorney, Agent, or Firm—Hill, Steadman & Simpson

[57] ABSTRACT

Ventilators and anesthetic systems are generally equipped with a number of different safety functions. An improved, manually operated safety valve device has a valve element, slideingly or rotatably arranged in a valve seat inside a valve body. The valve element is connected to an operating element. In a sliding embodiment, when the operating element is not actuated the valve element is retained in a first position by a spring, which presses against the operating element. When the operating element is partly depressed, a gas channel is exposed to an input channel and gas can pass to an output channel at a first defined flow rate. The operating element can be affixed in this position by means of an arresting unit. If a larger flow of gas is needed, the operating element can be completely depressed, whereupon a flow-through channel with a lower resistance to flow opens to pass a second defined flow of gas. In a rotating embodiment, the degree of rotation of the valve element results in the same functions as the extent of depression in the sliding embodiment.

11 Claims, 4 Drawing Sheets

VENTILATOR ANESTHETIC SYSTEM HAVING A MANUALLY OPERATED SAFETY VALVE DEVICE

BACKGROUND OF THE INVENTION

1. Field of the Invention

The present invention as directed to a safety valve devise suitable for use in a ventilator/anesthetic system.

2. Description of the Prior Art

The main task of a ventilator/anesthetic system is to support or maintain a patient's respiration. It is thus of the utmost importance for the ventilator/anesthetic system to be equipped with a plurality of safety functions. For example, the system normally incorporates a battery to provide power in the event of a power failure. Some systems also have separate emergency gas cylinders in case piped gas supplies should fail. Many ventilator/anesthetic systems contain manually operated safety valve devices used if the ventilator/anesthetic system's automatic valve systems break down.

A ventilator/anesthetic system having a manually operated safety valve device is known wherein safety valve device has a valve body with an input channel connected to a gas source, an output channel connected to a breathing gas circuit in the ventilator/anesthetic system, a flow-through channel with a first flow resistance. A valve seat and a valve element, moveable in relation to the valve seat, are disposed in the valve body in the flow-through channel, the valve element being in a first position in relation to the valve seat when the safety valve device is not actuated, at which first position no gas flows through the safety valve device. When manually operated, the valve element can be moved to a second position in relation to the valve seat, at which second position the flow-through channel opens to permit the passage of a first gas flow, whose magnitude depends on the first flow resistance, from the input channel to the output channel.

A safety valve device with a plurality of functions is also known. In anesthetic systems, for example, the safety valve device can be used to rapidly flush anesthetic gases out of the breathing gas circuit by supplying a relatively large flow of oxygen. The same safety valve device can also be used in emergency situations. A hand ventilator, usually a collapsible bag, is then connected to the breathing gas circuit. By pressing the valve briefly the hand ventilator fills with fresh oxygen. The physician can supply this oxygen to the patient by manually squeezing the hand ventilator. After a number of breaths, the hand ventilator must be emptied of used gas and is refilled with oxygen by pressing the safety valve device again.

In emergency situations, the ability to supply a continuous and relatively small flow of e.g. oxygen, in relation to the flushing flow, to the breathing gas circuit and the patient would be desirable. In principle, this could be achieved by installing an additional, manually operated valve device, but this would require more connectors and connections between gas lines, resulting in a more expensive and complex ventilator/anesthetic system and may even increase the risk of leaks in the system.

SUMMARY OF THE INVENTION

An object of the present invention is to achieve a ventilator/anesthetic system with a manually operated safety valve device capable of performing a plurality of functions, such as, e.g., passing different gas flows.

One such ventilator/anesthetic system is achieved according to the invention in a safety valve device as first described above further having a gas channel in the valve body with a second flow resistance which is larger than the aforementioned resistance first flow, this gas channel connecting the input channel to the output channel when the valve element is manually moved to a third position, so a second flow of gas, less than the first flow of gas, passes from the input channel to the output channel.

With such a safety valve device, the physician is able to open the device, by moving the valve element to the second position, to permit the passage of a large flow of, e.g., oxygen and open the device, by moving the valve element to the third position, to permit the passage of a smaller flow of oxygen.

It is advantageous if the safety valve device further includes an operating element, which is mechanically connected to the valve element in order to facilitate manual operation of the valve element, and a spring which loads the operating element automatically assumes the first position when there is no manual actuation. Since the safety valve device is only intended for use in extreme situations and then only after manual operation, it is advantageous for the safety valve device to be designed in this manner so it automatically assumes the first position.

In conjunction herewith, it is advantageous for the safety valve device to further include an arresting unit for affixing the valve element in the third position. Continuous passage of the smaller flow of gas is desirable. Operating the safety valve device is easier for the physician if it has an arresting unit for the third position, since the physician, or some other staff member, will not then need to hold the valve element (or the operating element) manually fixed in the third position.

In an embodiment of the ventilator/anesthetic system according to the invention, the valve seat is devised with a cylindrical cavity having a first defined diameter and the valve element is cylindrical and is movably arranged inside the cavity of the valve seat.

The anesthetic system can be advantageously devised so the valve element is slidably arranged inside the valve seat, the valve element being equipped with a first O-ring serving as a seal between the input channel and the output channel when the valve element is in its first position. The valve element has a portion with a second defined diameter which is smaller than the first defined diameter. A tubular channel in the valve body between the valve element and the valve seat forms the flow-through channel. The valve element, when the safety valve device is manually operated, is first moved to the third position, at which the gas channel connects the input channel to the output channel, and is then moved to the second position, at which the flow-through channel connects the input channel to the output channel.

A sliding construction for the valve element inside the valve seat facilitates manual actuation of the operating element. Locating the third position between the first and the second positions facilitates the valve element's construction, since the third position is to pass a smaller flow of gas than in the second position and must therefore offer greater resistance to the flow of gas.

The gas channel can advantageously be devised as a groove with a defined cross-sectional area and length in the valve seat. The groove's cross-sectional area and length govern its resistance to flow and therefore define the flow which can pass when the valve element is moved to the third position.

Alternatively, the gas channel can be devised in the valve element, whereby the gas channel has a first orifice and a second orifice on the surface of the valve element.

The first orifice is preferably located next to the first O-ring which serves as a seal between the input channel and the first orifice when the valve element is in its first position. the second orifice is preferably located at a defined distance from the first orifice and a second O-ring is arranged between the first orifice and the second orifice to serve as a seal between the input channel and the flow-through channel when the valve element is in its third position.

This construction ensures that only the smaller flow passes through the valve device when the valve element is in the third position.

As an alternative to movingly arranged valve element, the valve element can advantageously be rotatingly arranged in the valve seat, the flow-through channel and the gas channel running radially through the valve element and at least in part at one defined angle to each other. The flow-through channel and the gas channel could thus share a common part.

It is advantageous for the second position to be located in one direction of rotation from the first position and the third position is located in the other direction of rotation from the first position. For example, the valve element can be devised with three channels radiating out from the center of the valve body at a 120° to each other. The input channel and the output channel are then also arranged at a 120° to each other but displaced e.g. 60° to the channels' orifices. Rotation of the valve element 60° then opens a connection makes it easier for the physician to select the desired flow through the safety valve by selecting the valve element's direction of rotation.

When an arresting unit is employed, it is advantageous for the operating element to have a recess, and the arresting unit to be a sliding disc which can be moved into the recess on the operating element when actuated to place the valve element in the third position, thereby affixing the operating element and valve element in the third position.

DESCRIPTION OF THE PREFERRED EMBODIMENTS

Figure 1:
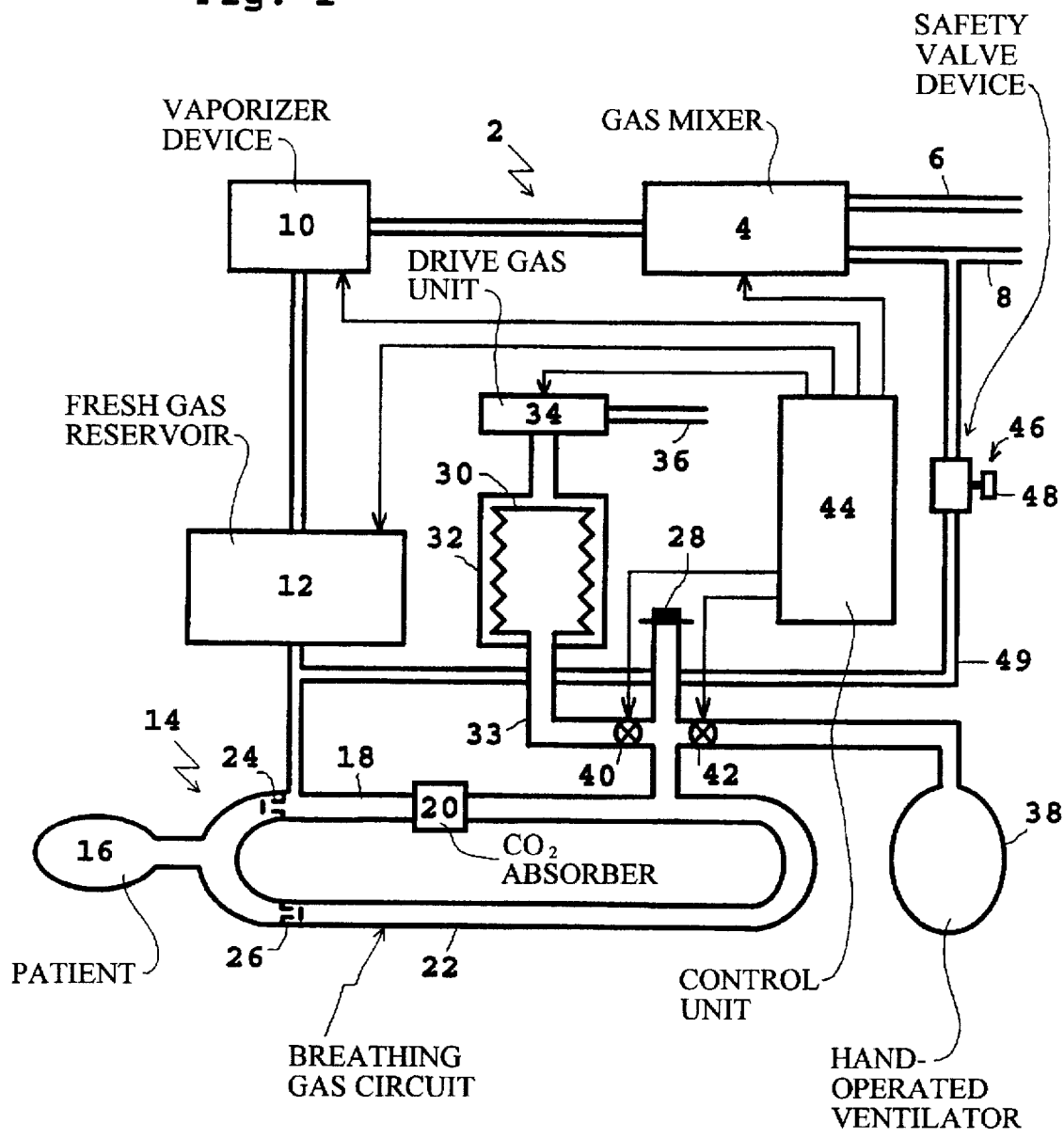
FIG. 1 schematically depicts an anesthetic system with a safety valve device according to the invention.

An anesthetic system 2 is shown in FIG. 1. The anesthetic system 2 includes a gas mixer 4, which receives nitrous oxide ($N_2O$) via a nitrous oxide connection 6 and oxygen ($O_2$) via an oxygen connection 8. $N_2O$ and $O_2$ are mixed in defined proportions in the gas mixer 4, and the mixed gas is sent to a vaporizer device 10. An anesthetic can be vaporized in the vaporizer device 10 and added to the gas mixture from the gas mixer 4 before the mixture is sent to a fresh gas reservoir 12. Gas from the fresh gas reservoir 12 is sent to a breathing gas circuit 14. The breathing gas circuit 14 is connected to a patient 16 who, in this instance, receives a gas mixture containing an anesthetic.

The breathing gas circuit 14 is a recirculating breathing gas circuit, i.e. the same breathing gas is reused immediately after expiration and returned to the patient through an inspiratory line 18 after passing a carbon dioxide ($CO_2$) absorber 20 which removes carbon dioxide from it. Expired gas passes from the patient 16 through an expiratory line 22. The direction of breathing gas flow in the breathing gas circuit 14 is governed by a first check (one-way) valve 24 and a second check valve 26. Surplus gas in the breathing gas circuit 14 is evacuated via a pressure relief valve 28 which also ensures that pressure in the breathing gas circuit 14, accordingly in the patient's lungs 16, does not become excessive. The removed gas is preferably sent to some form of evacuation device (not shown).

The respiration of the patient 16 can be controlled according to two different principles. The first employs a bellows 30 placed in a container 32. The gas space in the bellows 30 is connected to the breathing gas circuit 14 via a gas line 33, and the space between the bellows 30 and the wall of the container 32 is connected to a drive gas unit 34 which receives a drive gas through a drive gas connection 36. When an inspiration is to be imposed on the patient 16, the space between the bellows 30 and the wall of the container 32 is filled, compressing the bellows 30 and forcing breathing gas through the inspiratory line 18 and the $CO_2$ absorber to the patient 16. During expiration, gas is released from the space between the bellows 30 and the wall of the container 32, whereupon gas flows into the bellows 30 via the expiratory line 22 and the gas line 33.

The second principle is based on the use of a hand operated ventilator 38, preferably in the form of bag. The anesthesiologist can, by manually squeezing the gas-filled hand operated ventilator 38, force breathing gas to flow through the inspiratory line 18 to the patient 16. Expiration occurs when the physician releases his or her pressure on the hand operated ventilator 38, whereupon the hand ventilator fills with gas from the expiratory line 22. The choice of a regulatory principle for the imposed respiration is made with a first switching valve 40 and a second switching valve 42. For mechanically controlled respiration, the first switching valve 40 is open, and the second switching valve 42 is closed. The reverse applies for manually controlled respiration. The switching valves 40 and 42 are designed so the first switching valve 40 closes and the second switching valve 42 opens when there is a complete power failure and only manual ventilation of the patient 16 is possible.

All the components in the anesthetic system 2 are controlled and regulated by a control unit 44. The control unit 44 therefore regulates the mixture of nitrous oxide and oxygen in the gas mixer 4, the supply of anesthetic to the vaporizer device 10, the supply of fresh gas to the breathing gas circuit 14 from the fresh gas reservoir 12, the patient's breathing cycles via the drive gas unit 34 and switching between mechanical ventilation and manual ventilation with the first switching valve 40 and the second switching valve 42.

In case the anesthetic system 2 stops working for some reason, or for use if the physician should wish to give the patient 16 an extra dose of oxygen or quickly flush anesthetic out of the breathing gas circuit 14, the anesthetic system 2 is equipped with a manual safety valve device 46. The physician can operate the safety valve device 46 by pressing a pushbutton 48. The safety valve device 46 is connected to the oxygen connection 8 and to the breathing gas circuit 14 via a connecting line 49.

Figure 2:
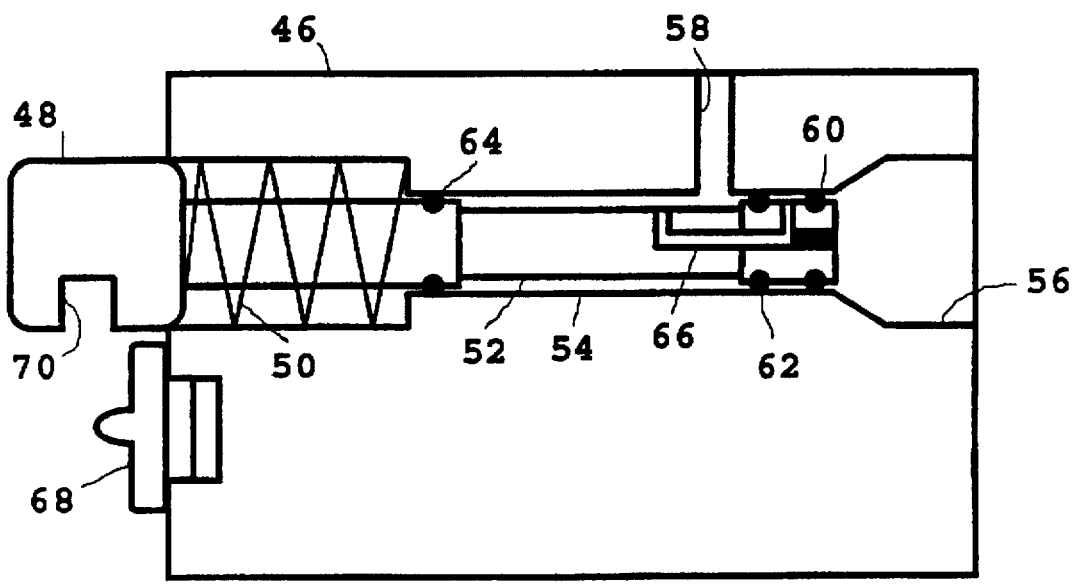
FIG. 2–4 show a first embodiment of the safety valve device respectively in three different functional positions.
Figure 3:
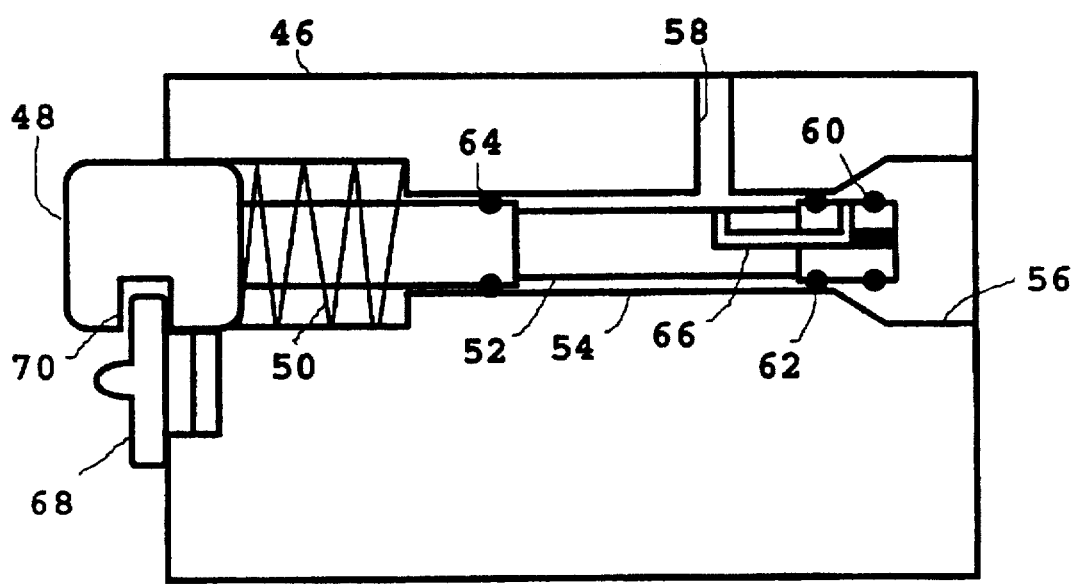
Figure 4:
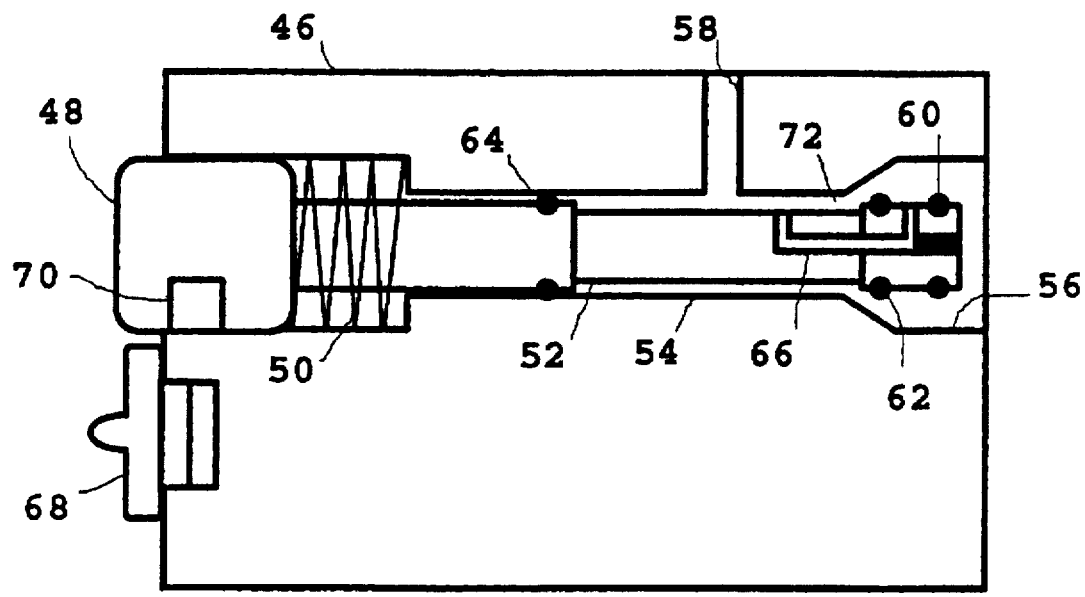

FIGS. 2–4, to which joint reference is made, show a first embodiment of the safety valve device 46 in the anesthetic system 2. The pushbutton 48 is slidably arranged in a valve body 46a the valve device 46 and acted on by a spring 50 so it normally is in a closed position. The pushbutton 48 is connected to a valve element 52, which is slidably arranged in a valve seat 54 in the valve body 46a. Connection to the oxygen line 8 occurs via an input channel 56 carrying pressurized oxygen. When the safety valve device 46 opens, oxygen flows through the valve body 46a and out through an output channel 58 connected to the connecting line 49. The valve element 52 is sealed against the valve seat 54 with a first O-ring 60, a second O-ring 62 and a third O-ring 64. There is a gas channel 66 in the valve body 52. The gas channel 66 has a small orifice in the surface of the valve body 52, and this gas channel 66 orifice is exposed to the oxygen in the input channel 56 when the pushbutton 48 is depressed a given distance, as shown in FIG. 3. Oxygen can then flow through the gas channel 66 to the output channel 58 at a rate governed by the flow resistance of the gas channel 66. Here, the second O-ring 62 provides a seal so gas can only flow through the gas channel 66. The safety gas device 46 is also equipped with a blocking button 68 which can be moved up into a recess 70 in the pushbutton 48 to affix the valve element 52 in this position.

If a large flow of oxygen is temporarily desired, e.g. to flush out the breathing gas circuit 14, this is easily accomplished when the physician pushes the pushbutton 48 completely in, as shown in FIG. 4. A flow-through channel 72 for oxygen then opens in the input channel 56. The flow-through channel 72 is arranged so its resistance to flow is less than that of the gas channel 66, so oxygen can therefore flow to the output channel 58 with a larger flow than when the valve element 52 is in the position shown in FIG. 3.

Figure 5:
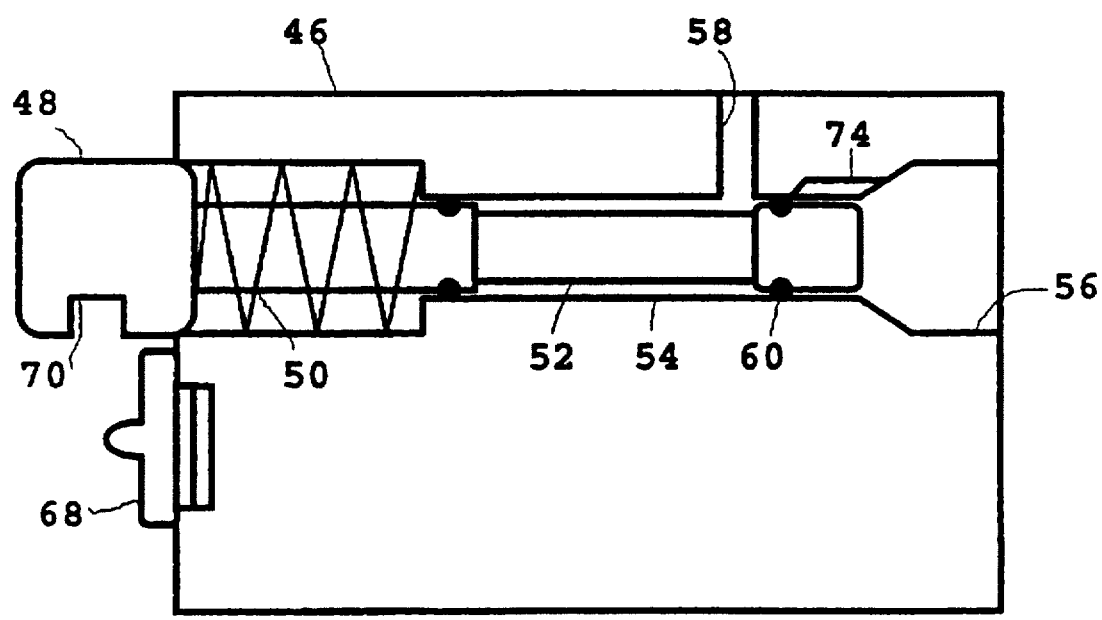
FIG. 5 shows a second embodiment of the safety valve device of the invention.

The safety valve device 46 can be devised in a number of different ways. FIG. 5 shows a second embodiment of the safety valve device 46. The second embodiment of the safety valve device 46 is a variant of the first embodiment shown in FIGS. 2-4, so the same designations have been used for the corresponding parts in FIG. 5. The main difference between the first embodiment and the second embodiment is in the introduction of a gas channel 74 inside the valve seat 54 of the second embodiment (FIG. 5) to permit the passage of a smaller flow of gas from the input channel 56 to the output channel 58 when the pushbutton 48 is only partially depressed. Here, only one O-ring 60 is needed on the valve element 52 to seal the input channel 56 and the output channel 58 from each other. The cross-sectional area and length of the gas channel 74 governs the resistance to flow which, in turn, governs the magnitude of the flow through the safety valve device 46. In practice, this flow is established at the time the safety valve device 46 is manufactured, the gas channel 74 being made with a specific area and length. In principle, the same flow can be achieved with a number of smaller grooves whose total flow resistance is the same as the defined flow resistance.

Other embodiments containing a sliding valve element inside the valve seat are also conceivable. For example, the input channel and the output channel can be arranged so they are opposite one another, and the valve element can be supplied with two radially arranged through openings with different dimensions which are sealed from each other and from the input channel with O-rings. The openings can be individually exposed to the input channel, when the valve element is moved, and release two different gas flows. As an alternative to through openings, the valve element can be devised with different diameters in order to pass the respective flow.

Figure 6:
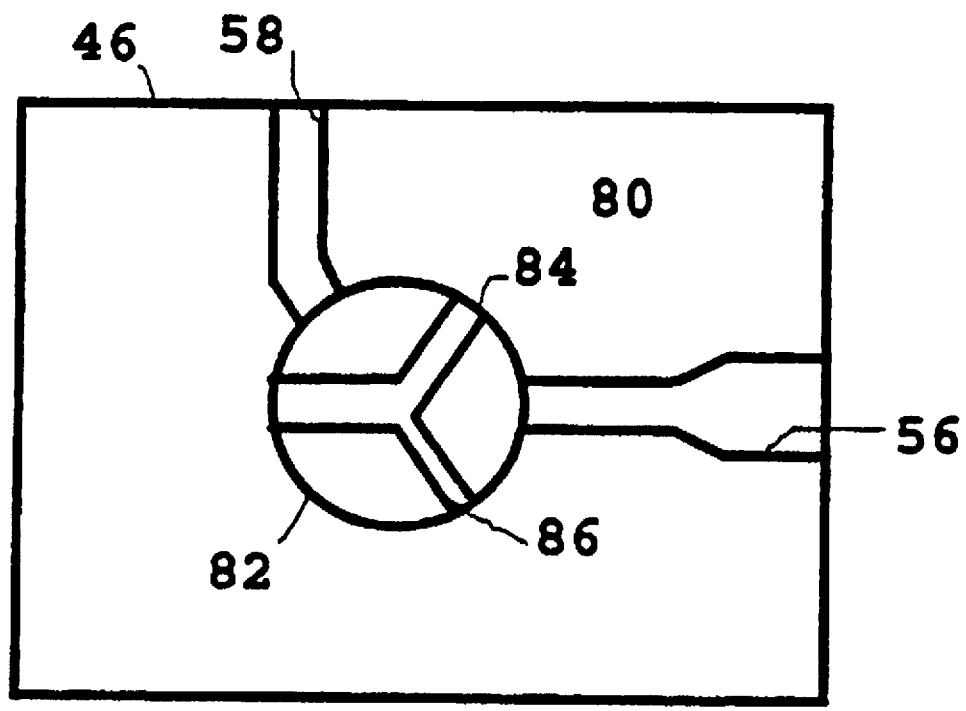
FIG. 6 shows a third embodiment of the safety valve device of the invention.

Another variant of the safety valve device 46, which does not employ a slidable valve element, is shown in FIG. 6, in which a third embodiment of the safety valve device 46 is shown. A valve element 82 is rotatingly arranged inside a valve seat 80. In the position shown in FIG. 6, corresponding to a nonactuated position, no gas passes from the input channel 56 to the output channel 58. A through channel 84 will open a connection between the input channel 56 and the output channel 58 when the valve element 82 is turned clockwise. This position could be e.g. spring-loaded so the valve element 82 returns to its first position as soon as actuation of the valve element 82 ceases. If the valve body 82 is instead turned counter-clockwise, a gas channel 86 opens through which a smaller flow of oxygen can flow, corresponding to the position in FIG. 3 for a slidable valve element. As in the previously described embodiments, the valve element 82 in FIG. 6 can be connected to a rotating button which can be affixed in the third position, i.e. when a flow of gas passes through the gas channel 86 from the input channel 56 to the output channel 58.

A number of alternative structures for the rotating valve element will be apparent to those skilled in the art. The safety valve device could also be devised so the valve element is both moveable and rotatable in the valve seat in order to assume the two different positions. The main principle of the invention, however, is a ventilator/anesthetic system containing a safety valve device which is able, in one position, to pass a first defined flow of a gas and, in a second position, to pass a second defined flow of gas which is smaller than the first defined flow.

Although modifications and changes may be suggested by those skilled in the art, it is the intention of the inventors to embody within the patent warranted hereon all changes and modifications as reasonably and properly come within the scope of their contribution to the art.

I claim as my invention:

1. In a ventilator/anesthetic system having a gas source and a breathing gas circuit, the improvement of a manually operated safety valve device comprising:

A valve body having an input adapted for connection to said gas source and an output adapted for connection to said breathing gas circuit with a first flow-through channel in said valve body between said input and said output;

said first flow-through channel having first flow resistance;

a valve seat disposed in said valve body in said first flow-through channel;

a valve element mounted in said valve body so as to be moveable relative to said valve seat between an unactuated, first position relative to said valve seat wherein said valve element does not permit gas to flow through said first flow-through channel and a manually actuated, second position relative to said valve seat wherein said valve element permits a first gas flow through said first flow-through channel, said first gas flow having a magnitude dependent of said first flow impediment;

said valve body having a second flow-through channel therein between said input and said output;

said second flow-through channel having a second flow resistance larger than said first flow resistant; and said valve element being mounted in said valve body for assuming a manually actuated, third position relative to said second flow-through channel for permitting a second gas flow dependent on said second flow resistance, said second gas flow being less than said first gas flow, to pass through said second flow-through channel.

2. The improvement of claim 1 further comprising manually actuatable operating means, mechanically connected to said valve element, for moving said valve element among said first, second and third positions, and spring bias means for loading said operating means and said valve element for maintaining said valve element in said first position in the absence of manual actuation of said operating means.

3. The improvement of claim 1 further comprising means in said valve body for holding said valve element in said third position after said valve element is manually actuated into said third position.

4. The improvement of claim 1 wherein said valve seat comprises a cylindrical cavity in said valve body having a diameter, and wherein said valve element comprises a cylindrical element disposed for longitudinally moving inside said cylindrical cavity.

5. The improvement of claim 4 wherein said valve element is disposed in said valve body for slidable movement along said longitudinal direction relative to said valve seat, and wherein said diameter of said cylindrical cavity comprises a first diameter, and the improvement further comprising an O-ring carried on said valve element and forming a seal between said input and said output when said valve element is in said first position, and said valve element having a second diameter which is smaller than said first diameter, said first flow-through channel comprising a tubular channel extending between said valve element and said valve seat, and said valve element, when manually actuated, being first moved to said third position, at which said second flow-through channel connects said input and said output, and upon further manual actuation said valve being moved to said second position, at which said first flow-through channel connects said input and said output.

6. The improvement of claim 5 wherein said second flow-through channel comprises a groove having a predetermined cross-sectional area and length in said valve seat.

7. The improvement of claim 5 wherein said second flow-through channel is disposed in said valve element, said second flow-through channel having a first orifice and a second orifice disposed on a surface of said valve element.

8. The improvement of claim 7 wherein said first orifice is disposed next to said O-ring, said O-ring forming a seal between said input and said first orifice when said valve element is in said first position, the improvement further comprising a further O-ring disposed between said first orifice and said second orifice, and said second orifice being disposed a distance from said first orifice so that said further O-ring provides a seal between said input and said first flow-through channel when said valve element is in said third position.

9. The improvement of claim 4 wherein said valve element is rotatingly disposed in said valve seat and wherein said first flow-through channel extends radially through said valve element, said second flow-through channel extends radially through said valve element, and a portion of said first flow-through channel and a portion of said second flow-through channel are oriented at a none-zero angle relative to each other.

10. The improvement of claim 9 wherein said valve element is mounted in said valve body for rotation relative to said valve seat in first and second opposite directions of rotation, with said second position being reachable by rotation of said valve element in said first direction from said first position, and said third position being reachable by rotation of said valve element in said second direction from said first position.

11. The improvement of claim 3 wherein said operating means comprises an operating element having a recess therein, and further comprising a sliding disc mounted in said valve body for movement into said recess when said operating element is manually actuated to place said valve element in said third position, thereby fixing said operating element and said valve element in said third position.

\* \* \* \* \*